United States Patent [19]

Chamberlin

[11] 3,962,235

[45] June 8, 1976

[54] PROCESS FOR MAKING α-CHLORINATED DERIVATIVES OF 2-ALKYL-2-OXAZOLINES AND 2-ALKYL-5,6-DIHYDRO-4H-OXAZINES

[75] Inventor: Thomas A. Chamberlin, Midland, Mich.

[73] Assignee: The Dow Chemical Company, Midland, Mich.

[22] Filed: Jan. 25, 1974

[21] Appl. No.: 436,780

[52] U.S. Cl. .......................... 260/244 R; 260/307 R
[51] Int. Cl.$^2$ .............. C07D 265/08; C07D 273/00; C07D 290/00
[58] Field of Search .................................. 260/244

[56] References Cited
OTHER PUBLICATIONS

Chem. Abst., 63, 13018(b), (1965),—Fell & Kung.
Chem. Abst., 65, 609(h), (1966)—Martin et al.
Chem. Abst., 66, 94933(u), (1967)—Aufderhaar et al.
The Merck Index, 7th Ed., —Merck & Co. Inc.—1960, p. 181.
Chem. Abst., 73, 45495(p) (1970)—Scherer et al.
Chem. Abst., 66, 94457(s), (1967)—Walling et al.

*Primary Examiner*—Jerome D. Goldberg
*Assistant Examiner*—D. W. Robinson
*Attorney, Agent, or Firm*—L. Wayne White

[57] ABSTRACT

The title compounds are prepared by contacting in liquid phase a 2-alkyl-2-oxazoline or oxazine with a t-alkyl hypochlorite. As an example, 2-chloromethyl-2-oxazoline was prepared in approximately 95 percent yield by contacting a substantially equimolar amount of 2-methyl-2-oxazoline with t-butyl hypochlorite for 19 hours at 23°C in the dark. The process was conducted in carbon tetrachloride solution.

12 Claims, No Drawings

PROCESS FOR MAKING α-CHLORINATED DERIVATIVES OF 2-ALKYL-2-OXAZOLINES AND 2-ALKYL-5,6-DIHYDRO-4H-OXAZINES

BACKGROUND OF THE INVENTION

The title compounds are known compounds which have been described, for example, by Ernst Aufderhaar et al. in Justus Liebigs Ann. Chem. 701, 166–173 (1967) (C.A. 66: 94933u) and by Otto Scherer et al. in South African Pat. No. 6904,551 (C.A. 73: 45495p). Such compounds were used as comonomers in forming films, coatings, and injected molded articles as described in French Patent of Addition No. 91,744 (C.A. 70: 115724b) and German Pat. No. 1,206,585 (C.A. 64: 6783a). The 2-chloromethyl-2-oxazoline and 2-chloromethyl-5,6-dihydro-4H-oxazine derivatives are the most common species in this genus of compounds.

The title compounds were conventionally prepared in relatively low yield by reacting the 2-alkyl oxazoline or oxazine compounds with chlorine in the presence of an acid acceptor. Aufderhaar illustrates this procedure.

SUMMARY OF THE INVENTION

I have discovered a novel process for making the α-chlorinated derivatives of 2-alkyl-2-oxazolines and 2-alkyl-5,6-dihydro-4H-1,3-oxazines in extremely high yields. The process comprises reacting by contacting in liquid phase (a) a 2-alkyl-2-oxazoline or a 2-alkyl-5,6-dihydro-4H-1,3-oxazine with (b) a t-alkyl hypochlorite.

The tertiary alkyl hypochlorites are extremely reactive compounds and it was most surprising to find that they would selectively chlorinate the α-carbon atom of the 2-alkyl substituent on the oxazoline and oxazine reactants.

DETAILED DESCRIPTION OF THE INVENTION

The instant process is conducted by blending the reactants together in liquid phase. This may be done by blending the reactants neat or in the presence of an inert organic solvent. The process is preferably conducted in the presence of an inert organic solvent. By "an inert organic solvent" is meant any organic compound which is not reactive under the process conditions with either the oxazoline or oxazine reactant or with the t-alkyl hypochlorite reactant. Suitable such solvents therefore include carbon tetrachloride, methyl chloroform, difluorotetrachloroethane, cyclohexane, benzene, and the like. Carbon tetrachloride is currently the solvent of choice due to its commercial availability and cost.

The reaction temperature and pressure may be varied to convenience so long as the reacting mixture is maintained in substantially liquid phase and below the thermal decomposition temperature of the t-alkyl hypochlorite. Satisfactory reaction rates are normally achieved at reaction temperatures varying from about 25° up to about 75°C at atmospheric pressure.

The process may be conducted in the presence or absence of actinic light, with the latter condition being preferred.

The ratio of reactants may be varied but substantially stoichiometric amounts of reactants are preferred. The stoichiometry of the reaction, of course, requires one mole of t-alkyl hypochlorite per hydrogen atom to be replaced on the α-carbon atom of the 2-alkyl-2-oxazoline or 2-alkyl-5,6-dihydro-4H-1,3-oxazine reactant.

The reactants in this process are well known classes of compounds. The oxazoline and oxazine reactants each bear a 2-alkyl substituent of from 1 to about 12 carbon atoms or more. The alkyl substituent must, of course, have replaceable hydrogen atoms and it is normally a straight chain alkyl group. The oxazoline and oxazine reactants are normally prepared by reacting an alkanoic acid with an ethanolamine or a propanolamine to form the amine salt or carboxamide which is subsequently dehydrated to give the oxazoline or oxazine product. Methods of preparation are discussed by Wiley et al. in Chemical Reviews, Volume 44, 447-476 (1949), by Seeliger et al. in Angew. Chem. Internat. Edit. Volume 5, No. 10 (1966), and by Frump in Chemical Reviews (1971), Vol. 71, 483–505. The oxazoline and oxazine reactants may, in addition to the 2-alkyl substituent, bear one or more substituents on the heterocyclic ring carbon atoms. The ring-unsubstituted reactants, however, are preferred and the 2-methyl-2-oxazoline is the most preferred reactant.

The t-alkyl hypochlorites are likewise a known class of reactants, each member of which contains the radical —OCl attached to a tertiary carbon atom. They have been prepared by reacting chlorine monoxide with a tertiary alcohol in carbon tetrachloride solution, by reacting hypochlorous acid with tertiary alcohols in carbon tetrachloride, and by a variety of other techniques described in the prior art. Representative examples of the known class of tertiary alkyl hypochlorites include those corresponding to the formula

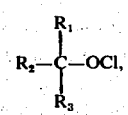

wherein $R_1$–$R_3$ have the values assigned in Table 1:

Table 1

| $R_1$ | $R_2$ | $R_3$ |
|---|---|---|
| $CH_3$ | $CH_3$ | $CH_3$ |
| $CH_3$ | $CH_3$ | $C_2H_5$ |
| $CH_3$ | $CH_3$ | $n\text{-}C_4H_9$ |
| $CH_3$ | $CH_3$ | $n\text{-}C_5H_{11}$ |
| $CH_3$ | $CH_3$ | $n\text{-}C_6H_{13}$ |
| $CH_3$ | $CH_3$ | $-CH_2-_4C_6H_5$ |
| $CH_3$ | $C_2H_5$ | $C_2H_5$ |
| $CH_3$ | $n\text{-}C_3H_7$ | $n\text{-}C_4H_9$ |
| $CH_3$ | $CH_3$ | $CH_2CH(CH_3)_2$ |
| $CH_3$ | $n\text{-}C_3H_7$ | $CH_2CH_2CH(CH_3)_2$ |
| $C_2H_5$ | $C_2H_5$ | $n\text{-}C_3H_7$ |

Cyclic t-alkyl hypochlorites are included within the term t-alkyl hypochlorites and they are derived from cyclic t-alkanols. Illustrative such compounds include those corresponding to the formulas

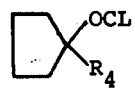 and 

wherein $R_4$ is an alkyl group, such as methyl, ethyl, propyl, butyl, hexyl, and the like. t-Butyl hypochlorite is the most preferred t-alkyl hypochlorite for use herein.

The following examples further illustrate the invention.

EXAMPLES 1–3

Reaction of 2-Methyl-2-Oxazoline with t-Butyl Hypochlorite

2-Methyl-2-oxazoline and t-butyl hypochlorite were blended in carbon tetrachloride and were maintained in the dark with stirring for periods of time and temperatures as set forth in Table 2 below. The products were identified by gas phase chromatography, using known compounds as standards as well as by boiling point and spectroscopic methods.

Table 2

| Ex. | Reactant Ratio* | Temperature (°C) | Time (Hours) | Product (%)* | | | |
|---|---|---|---|---|---|---|---|
| | | | | A | B | C | D |
| 1 | 1 | 23 | 19 | 0 | 95.6 | 4.4 | 0 |
| 2 | 2 | 57 | 3 | 0 | 8.9 | 91.1 | 0 |
| 3 | 3 | 57 | 20 | 0 | 4.5 | 92.8 | 2.8 |

*Reactant ratio represents the moles of t-butyl hypochlorite present per mole of oxazoline reactant.

*Product A is 2-methyl-2-oxazoline; Product B is 2-chloromethyl-2-oxazoline; Product C is 2-dichloromethyl-2-oxazoline; and Product D is 2-trichloromethyl-2-oxazoline.

EXAMPLES 4–5

Reaction of 2-ethyl-2-Oxazoline with t-Butyl Hypochlorite

In like manner 2-ethyl-2-oxazoline was reacted with t-butyl hypochlorite in carbon tetrachloride in the dark. The reaction mixture was maintained in each instance at 57° for 28 hours with continuous stirring. In Example 4, equimolar amounts of reactants were used. In Example 5, there were 2 moles of hypochlorite per mole of oxazoline. The results are summarized in Table 3 below. Again product identification was by gas phase chromatography.

Table 3

| Ex. | Product (%)* | | |
|---|---|---|---|
| | E | F | G |
| 4 | 7.6 | 90.9 | 1.5 |
| 5 | 3.1 | 94.7 | 2.3 |

*Product E was unreacted 2-ethyl-2-oxazoline; Product F was 2-(α-chloroethyl)-2-oxazoline; and Product G was 2-(α,α-dichloroethyl)-2-oxazoline.

EXAMPLES 6–8

Reaction of 2-Methyl-5,6-Dihydro-4H-Oxazine with t-Butyl Hypochlorite

In like manner 2-methyl-5,6-dihydro-4H-oxazine was reacted with t-butyl hypochlorite in carbon tetrachloride in the dark for 44 hours at 57°C. The results were tabulated in Table 4.

Table 4

| Ex. | Reactant Ratio* | Product Yield (%)* | | | |
|---|---|---|---|---|---|
| | | H | I | J | K |
| 6 | 1 | 0 | 92.1 | 7.9 | 0 |
| 7 | 2 | 0 | 8.5 | 91.5 | 0 |
| 8 | 3 | 0 | 0 | 97.7 | 2.3 |

*Reactant Ratio is moles of t-butyl hypochlorite used per mole of oxazine reactant.

*Product H was unreacted oxazine; Products I-K were 2-chloromethyl-, 2-dichloromethyl- and 2-trichloromethyl- and 2-trichloromethyl-5,6-dihydro-4H-oxazine, respectively.

I claim:

1. A process for making α-chlorinated derivatives of 2-alkyl-2-oxazolines and 2-alkyl-5,6-dihydro-4H-oxazines comprising reacting by contacting in liquid phase (a) a 2-alkyl-2-oxazoline or a 2-alkyl-5,6-dihydro-4H-oxazine with (b) a t-alkyl hypochlorite at a temperature below the thermal decomposition temperatures of said t-alkyl hypochlorite.

2. The process defined by claim 1 wherein (a) is 2-alkyl-2-oxazoline or 2-alkyl-5,6-dihydro-4H-oxazine.

3. The process defined by claim 2 wherein said alkyl is a straight chain alkyl group of from 1 to 12 carbon atoms.

4. The process defined by claim 3 wherein said alkyl group is methyl.

5. The process defined by claim 1 wherein (b) is t-butyl hypochlorite.

6. The process defined by claim 1 wherein the reaction temperature is from about 25° to about 75°C.

7. The process defined by claim 1 wherein said process is conducted in an inert organic solvent.

8. The process defined by claim 7 wherein said solvent is carbon tetrachloride.

9. The process defined by claim 3 wherein (a) is 2-methyl- or 2-ethyl-2-oxazoline or 2-methyl-5,6-dihydro-4H-oxazine and (b) is t-butyl hypochlorite and wherein said process is conducted in carbon tetrachloride at a reaction temperature of from about 25° to about 75°C and in the absence of actinic light.

10. The process defined in claim 9 wherein (a) is 2-methyl-2-oxazoline and wherein essentially equimolar amounts of (a) and (b) are present in the reaction mixture.

11. The process defined by claim 1 wherein said process is conducted in the absence of actinic light.

12. The process defined by claim 1 wherein (b) is present in the reaction mixture in essentially stoichiometric amounts, based on the number of hydrogen atoms to be replaced on the α-carbon atoms of the 2-alkyl substituent of (a).

* * * * *